(12) United States Patent
Wang et al.

(10) Patent No.: US 11,000,708 B2
(45) Date of Patent: May 11, 2021

(54) **USE OF CARRIMYCIN IN *MYCOBACTERIUM TUBERCULOSIS* INFECTION RESISTANCE**

(71) Applicant: SHENYANG FUYANG PHARMACEUTICAL TECHNOLOGY CO., LTD., Liaoning (CN)

(72) Inventors: Yiguang Wang, Liaoning (CN); Yang Jiang, Liaoning (CN); Xiaofeng Zhao, Liaoning (CN); Weiqing He, Liaoning (CN)

(73) Assignee: SHENYANG FUYANG PHARMACEUTICAL TECHNOLOGY CO., LTD., Liaoning (CN)

( * ) Notice: Subject to any disclaimer, the term of this patent is extended or adjusted under 35 U.S.C. 154(b) by 0 days.

(21) Appl. No.: 16/067,327

(22) PCT Filed: Dec. 5, 2016

(86) PCT No.: PCT/CN2016/108502
§ 371 (c)(1),
(2) Date: Jun. 29, 2018

(87) PCT Pub. No.: WO2017/114095
PCT Pub. Date: Jul. 6, 2017

(65) Prior Publication Data
US 2019/0001160 A1    Jan. 3, 2019

(30) Foreign Application Priority Data

Dec. 31, 2015  (CN) .......................... 201511030787.7

(51) Int. Cl.
*A61P 31/06* (2006.01)
*A61K 31/7048* (2006.01)
*A61K 9/00* (2006.01)
*A61K 31/496* (2006.01)

(52) U.S. Cl.
CPC ............ *A61P 31/06* (2018.01); *A61K 9/0019* (2013.01); *A61K 9/0053* (2013.01); *A61K 31/496* (2013.01); *A61K 31/7048* (2013.01)

(58) Field of Classification Search
CPC ...... A61P 31/06; A61P 9/0019; A61P 9/0053; A61P 31/496; A61P 31/7048
See application file for complete search history.

(56) References Cited

U.S. PATENT DOCUMENTS

| | | | | |
|---|---|---|---|---|
| 7,098,219 | B2 * | 8/2006 | de Souza | A61K 45/06 |
| | | | | 514/292 |
| 2008/0161249 | A1 * | 7/2008 | Huang | A61K 31/16 |
| | | | | 514/29 |
| 2013/0150316 | A1 * | 6/2013 | Jiang | A61K 31/7048 |
| | | | | 514/30 |

FOREIGN PATENT DOCUMENTS

| | | |
|---|---|---|
| CN | 1554355 A | 12/2004 |
| CN | 103142520 A | 6/2013 |
| CN | 105497053 A | 4/2016 |
| EP | 2 578 596 A1 | 4/2013 |
| JP | 2013-528167 A | 7/2013 |
| JP | 2014-104068 A | 6/2014 |
| WO | WO 2007/065637 A1 | 6/2007 |
| WO | WO 2008/122038 A1 | 10/2008 |

OTHER PUBLICATIONS

Lin et al., Antimicrobial Agents and chemotherapy, p. 2038-2044, Jan. 2014, vol. 58. No. 4, (Year: 2014).*
Lin et al., PNAS, Oct. 23, 2012, vol. 109, No. 473, pp. 17412-17417 (Year: 2012).*
Dai Jian-Lu et al., "Improvement of New Generation of Bitespiramycin Producing Strain by Microwave Radiation," Chinese Journal of Antibiotics, vol. 34, No. 7, Jul. 31, 2009, pp. 406-410 and 428. (6 pages).
Kanakeshwari Falzari, et al., "In Vitro and In Vivo Activities of Macrolide Derivatives against *Mycobacterium tuberculosis*", Antimicrobial Agents and Chemotherapy, Apr. 30, 2005, pp. 1447-1454, vol. 49, No. 4.
International Search Report (PCT/ISA/210) dated Feb. 28, 2017, by the Chinese Patent Office as the International Searching Authority for International Application No. PCT/CN2016/108502.
Written Opinion (PCT/ISA/237) dated Feb. 28, 2017, by the Chinese Patent Office as the International Searching Authority for International Application No. PCT/CN2016/108502.
Anuradha et al.,: "Fermentation, Isolation, Purification and Characterization of an Antitubercular Antibiotic From Streptomyces Luridus MTCC 4402", Indian Journal of Experimental Biology, Council of Scientific & Industrial Research, IN, vol. 54, Sep. 2016, pp. 577-585, XP009509172. (9 pages).
Extended European Search Report dated Nov. 21, 2018, issued by the European Patent Office in corresponding European Application No. 16880885.5. (7 pages).

(Continued)

*Primary Examiner* — Jean P Cornet
(74) *Attorney, Agent, or Firm* — Buchanan Ingersoll & Rooney PC

(57) ABSTRACT

Use of carrimycin in *Mycobacterium tuberculosis* infection resistance comprises the main steps: measuring the activity of carrimycin in *Mycobacterium tuberculosis* resistance by adopting an absolute concentration method through taking clinical first-line antituberculotics, i.e., isoniazid and rifampicin as controls. The result indicates that carrimycin has obvious superior activity to clinically-separated *Mycobacterium tuberculosis* including drug-resistant bacteria compared with those of the clinical first-line control drugs, i.e., the isoniazid and the rifampicin, and use of carrimycin in manufacturing drugs for treating tubercle *Bacillus* infected diseases are expected to be developed.

4 Claims, No Drawings

(56) References Cited

OTHER PUBLICATIONS

Office Action (Notice of Reasons for Refusal) dated Oct. 1, 2019, by the Japanese Patent Office in corresponding Japanese Patent Application No. 2018-553283 and English translation of the Office Action. (7 pages).

* cited by examiner

USE OF CARRIMYCIN IN MYCOBACTERIUM TUBERCULOSIS INFECTION RESISTANCE

TECHNICAL FIELD

The present disclosure relates to a use of macrolide antibiotics in treatment of tubercle *Bacillus* infections.

BACKGROUND

*Tuberculosis* is a chronic infectious disease resulting from *Mycobacterium tuberculosis* (MTB) infection. It mainly affects the lungs and is a disease with the most single-caused casualties among infectious diseases. *Tuberculosis* is common in people with low immunologic function and is a most-common opportunistic-infected disease related to AIDS (Acquired Immunodeficiency Syndrome). It was reported by World Health Organization (WHO) that 8 to 10 millions of phthisic cases newly appear all over the world every year, and 3 to 4 millions of people died of *tuberculosis*, and developing countries have more patients. In addition, it is predicted that from 2000 to 2020, about one billion of people will be infected, and 35 millions of people will die of *tuberculosis*. At the same time, MTB drug resistance increases with years and will become a major threat to *tuberculosis* control in the whole world. Our country is one of 22 countries with a high incidence of *tuberculosis* in the whole world, the number of patients suffering from active *tuberculosis* is ranked second in the world, and epidemical characteristics comprise high infection rate, high case rate, high drug resistance and high death rate, and ¼ or more of 2 millions of MTB positive patients in the whole country are tubercle *Bacillus* drug resistant patients.

At present, the first-line drugs commonly used for clinical treatment of *tuberculosis* (with definite *Mycobacterium tuberculosis* resistance activity) comprise 5 kinds, i.e., rifampicin, isoniazid, streptomycin, ethambutol and pyrazinamide. However, these drugs have many adverse reactions, are limited in bactericidal action. The course of treatment is relatively long, and they are usually used for more than 6 months. And patients have poor compliance. Second-line antituberculotics (with bacteriostasis action on *Mycobacterium tuberculosis*) comprise capreomycin, ethionamide, p-aminosalicylic acid, cycloserine, ciprofloxacin, amikacin, kanamycin, etc. However, these drugs have a greater adverse reaction, and the course of treatment is longer (18 to 24 months), the cost is expensive and the cure rate is lower. It is noteworthy that clinical researches show that all the first-line antituberculotics can cause injury to livers. For example: adverse reactions of isoniazid comprise peripheral neuritis, hepatotoxicity, central nervous system disorder and allergy. Adverse reactions of rifampicin comprise hepatotoxicity, digestive tract discomfort, neurological symptoms and allergy. An adverse reaction of ethambutol is mainly manifested by optic nerve toxicity. Adverse reactions of pyrazinamide comprise xanthochromia and blood uric acid content increase. Toxicity and bacterial drug resistance problems of streptomycin seriously limit the use of streptomycin, and the incidence rate of bacterial drug resistance can be reduced through jointly using the streptomycin with other drugs, although clinical uses are few, the streptomycin still serves as a first-line antituberculotic. [Zhu, shanmei, Strait Pharmaceutical Journal, 2010, 22 (2): 123-125] In addition, it was reported that researches on 518 clinically-separated *Mycobacterium tuberculosis* strains in 2010 show that among the first-line drugs, the highest resistance rate of *Mycobacterium tuberculosis* to isoniazid is 53.67%, and the resistance to streptomycin is 45.95%; among the second-line drugs, the resistance to ofloxacin reaches 39.77%, the resistance to amikacin is 15.83%, and the resistance to capreomycin is 21.81%; among 321 strains resistant to one or more first-line drugs, the resistance to ofloxacin reaches up to 57.01%, and the resistance to amikacin and the resistance to capreomycin are 25.55% and 33.02%, respectively; among 217 multiple-drug-resistant strains, the resistance to ofloxacin reaches 72.35% [Liu, Yidian, et al., Compilation of Academic conference on clinical foundation profession of Anti-*tuberculosis* Association of China in 2010, Page 274-275]. This brings about a severe challenge to implementation of *tuberculosis* control work, particularly multiple-drug-resistant *tuberculosis* control work in our country. Therefore, it is already urgent to find substitutes for resistance *Mycobacterium tuberculosis*, particularly multiple-drug-resistant strains as soon as possible.

New macrolide drugs, i.e., clarithromycin, azithromycin and roxithromycin are derivatives of 14-membered erythromycin, are different from the first-line and second-line antituberculotics in antibacterial action mechanism, are reversibly bound with 50S subunits of ribosome in thalli and interfere the synthesis of proteins. It is reported domestically that the MIC of clarithromycin to sensitive *Mycobacterium tuberculosis* is 0.25-2.0 micrograms/milliliter, and the MIC of clarithromycin to drug-resistant bacteria is 2.0-32 micrograms/milliliter; and the MIC of azithromycin against *Mycobacterium tuberculosis* is 128 micrograms/milliliter [Tang, Shenjie, latest progress of antituberculotic research, Anti-*tuberculosis* Journal of China, Page 1-3, supplement, Vol. 28, 2006]. It was reported abroad that the MIC of clarithromycin to *M. tuberculosis* H37Rv (ATCC 27294) is 6 micrograms/milliliter; the MIC of azithromycin is 95 micrograms/milliliter [Kanakeshwari Falzari et al: In vitro and in vivo activities of macrolide derivatives against *Mycobacterium tuberculosis*. Antimicrob. Agents and Chemother. 2005, 49(4): 1447-1454]; and the MIC of roxithromycin is greater than or equal to 64 micrograms/milliliter. This kind of drugs are not included in drugs for clinical treatment of *Mycobacterium tuberculosis* infections, but there are reports of clinical treatment of tubercle *Bacillus* infected diseases through using the drugs independently or using the drugs jointly with antituberculotics. [Xu, Li, et al., Investigation of application of antituberculotic related antibacterial drugs for Shenzhen inpatients, Anti-*tuberculosis* Journal of China, 2010, 32 (3): 151-154].

Proven by researches, 16-membered and 14-membered cyclomacrolide antibiotics have similar antibacterial action mechanisms. This kinds of drugs have low activity to *Mycobacterium tuberculosis*, for example, the MIC of tylosin to *M. tuberculosis* H37Rv (ATCC 27294) is 58.6 micrograms/milliliter, and both the MIC of spiramycin and the MIC of medemycin are greater than 100 micrograms/milliliter [Kanakeshwari Falzari et al: In vitro and in vivo activities of macrolide derivatives against *Mycobacterium tuberculosis*. Antimicrob. Agents and Chemother. 2005, 49(4): 1447-1454]. Therefore, there is no related report on clinical treatment of *tuberculosis* by using this kind of antibiotics at home and abroad so far.

A novel 16-membered macrolide antibiotic, i.e., carrimycin (Old name: shengjimycin and biotechspiramycin) developed by our laboratory is 4"-acylated spiramycin taking isovaleryl spiramycin as a major ingredient, and an action mechanism of the carrimycin is to inhibit protein synthesis by binding to ribosomes of the bacterial. Shown by in-vivo and in-vitro test results, carrimycin is effective to Grampositive bacteria, particularly some drug-resistant bacteria (e.g. β-lactam resistant *Staphylococcus aureus*, erythromycin resistant *Staphylococcus aureus*, etc.) and is free of obvious cross drug resistance with similar drugs. At the same time, carrimycin has very good antibacterial activity to *Mycoplasma* and *Chlamydia*, also has an antibacterial action on part of Gram-negative bacteria and also has a good antibacterial effect on *Toxoplasma, Legionella*, etc. [Wang, Yiguang, et al., "Biotechspiramycin and application thereof in infectious disease resistance", 23 Dec. 2003, China patent of disclosure: ZL 2003 1 0122420.9]. Carrimycin has good tissue penetrability, and the in-vivo antibacterial activity of carrimycin is obviously superior to in-vitro antibacterial activity. And carrimycin has a potential immunoregulation action. Proven by clinical researches of I, II and III stages, carrimycin is an antibiotic which is safe in use and remarkable in treatment effect. Out laboratory further develops potential effects of carrimycin, and the clinical indication and scope of use of carrimycin are enlarged.

SUMMARY

An object of the present disclosure is to provide a series of detections and experimental researches on activity of carrimycin to clinically-separated *Mycobacterium tuberculosis* to prove that carrimycin possibly has new use in treatment of tubercle *Bacillus* infected diseases.

According to the present disclosure, main steps are as follows: clinically-separated tubercle *Bacillus*, i.e., *Mycobacterium tuberculosis* resistance activity of carrimycin is measured by adopting an absolute concentration method, and clinically-used antituberculotic first-line drugs, i.e., isoniazid and rifampicin are taken as controls. Proven by experimental results, carrimycin shows activity to 172 strains of 240 clinically-separated *Mycobacterium tuberculosis* strains and has a total effective rate of 71.66%; 37 strains have activity superior to that of the isoniazid and account for 21.5% of effective strains; 39 strains have activity superior to that of the rifampicin and account for 22.7% of effective strains; and 23 strains have activity superior to that of the isoniazid and that of the rifampicin and account for 13.4% of effective strains. Results of the present disclosure show that new use of carrimycin in treatment of *Mycobacterium tuberculosis*, which is resistant to the isoniazid and the rifampicin, infected diseases is advantageously developed.

The present disclosure further provides a use of a composition in manufacturing drugs for treating tubercle *Bacillus* infected diseases, the composition comprises carrimycin as an active ingredient and a pharmaceutically acceptable carrier.

According to the use provided by the present disclosure, oral formulation, injection formulation or any other appropriate formulation can be used.

DETAILED DESCRIPTION

Embodiments below are only used for helping those skilled in the art to better comprehend the present disclosure, rather than limiting the present disclosure in any way.

In specific embodiments, a series of researches on measuring of *Mycobacterium tuberculosis* resistance activity of carrimycin are carried out by taking first-line antituberculotic used frequently in-clinic as controls. It is shown in the results that for clinically-separated *Mycobacterium tuberculosis*, the quantity of effective strains on which carrimycin effects is higher than those of control groups. The carrimycin is applied to treat some drug-resistant *Mycobacterium tuberculosis* infected diseases.

<Embodiment 1> Acquisition and Treatment of *Mycobacterium tuberculosis* Specimen According to the provisions of National Standard WS288-2008 <Pulmonary *tuberculosis* Diagnosis Standard> issued by Ministry of Health, patients, who are definitely diagnosed or highly suspected as *tuberculosis* by clinical manifestations, signs and chest imaging examinations are selected. About 2 mL of specimens of a sputum, hydrothorax, cerebrospinal fluid and pus from the selected patients were collected, and each specimen was added into a 50 mL centrifuge tube with a screw cap. An equal amount of N-acetyl-L-cysteine sodium hydroxide (NaOH-NALC) pretreatment solution was added into the centrifuge tube, and vortexing for 20 seconds. The oscillated material was allowed to stand for 18 minutes at room temperature. PBS (pH 6.8) was added until the volume is 40 mL, centrifuging at 3000 g for 20 minutes, and then the obtained supernatant was discarded and precipitates are reserved. 2 mL of PBS (pH 6.8) was added to prepare a suspension. A culture medium was inoculated with the treated specimen for solid culture.

<Embodiment 2> Isolation, Culture and Identification of *Mycobacterium tuberculosis* Specimen 1. Preparation of a Culture Medium:

Ingredients of the culture medium are as shown in a table 1. All the ingredients were added into distilled water according to listed dosage, and the ingredients were fully dissolved. Boiling for 30 minutes or 15 minutes under high pressure at the temperature of 121 DEG C.

Fresh chicken eggs were taken, washed with tap water, brushed with soap water to be clean, and wiped with 75% alcohol for disinfection after the chicken egg were drained. Egg fluid was poured into a sterilized graduated enameled cup under sterile operation, full stirring for uniform mixing. Then filtering the egg fluid conducted with a sterilization gauze. Then, adding 1000 mL filtered egg fluid to the culture medium, and full and uniform mixing. 20 mL of 2% malachite green was added, and full and uniform mixing; 7 mL of the total culture medium was added into a subpackage test tube (18 mm*180 mm), and coagulating was conducted for 50 minutes at the temperature of 85 DEG C. in a steam thermostat. The prepared culture medium was taken from the tube according to 5%, and cultured for 48 hours at the temperature of 37 DEG C. for sterile examination. And the culture medium was put in a refrigerator with the temperature of 4 DEG C. for later use after the sterile examination is qualified, and the culture medium is used in one month.

TABLE 1

| Culture Medium | |
|---|---|
| Ingredient | Dosage |
| Monosodium glutamate (purity: 99% or more) | 7.20 g |
| Potassium dihydrogen phosphate | 2.40 g |
| Magnesium sulfate | 0.24 g |
| Magnesium citrate | 0.60 g |
| Glycerine | 12 mL |
| Distilled water | 600 mL |

2. Inoculated Culture of Tubercle *Bacillus*

0.1 mL of Specimen treated in the <embodiment 1> was sucked, and was uniformly inoculated on a slant face of the culture medium. The entire slant face was covered with the suspension. The inoculated slant face of the culture medium was cultured in an incubator at the temperature of 37 DEG C. Growth conditions of bacteria were observed on third day and seventh day, then, observing was conducted once per week. Positive suspects were picked out timely if the positive suspects were discovered, and observing was conducted every day. Positive growth was verified through smear straining. It is determined that *Mycobacterium tuberculosis* culture is negative if growth of bacteria is absent through 8 weeks of culture.

3. Acid-Resistance Staining of Tubercle *Bacillus*

Taking a small amount of positive strains of *Mycobacterium tuberculosis* cultured, and the strain evenly was coated on slides, fixed on flames, stained with stony carbonic acid solution, heated on flames for 5 minutes, decolorized with 3% hydrochloric acid for about 1 minute, and rinsed with water. And then after being counterstained with alkaline methylene solution for 1 minute, the strain was rinsed with water, blotted dry, and observed under the oil microscope. The stained red was *Mycobacterium tuberculosis.*

<Embodiment 3> Experiment of *Mycobacterium tuberculosis* Resistance Activity of Carrimycin 1. Absolute Concentration Method 1) Antituberculotics Carrimycin standard products: derived from National Institute for the Control of Pharmaceutical and Biological Products; control drugs: isoniazid and rifampicin purchased from standard products of Sigma. Required dosages (table 2) are prepared through preparing mother solutions from the antituberculotics according to certain concentrations and then adding a culture medium according to certain amount.

2) Strains Inoculation

Clinical-specimen-separated strains were confirmed to be a culture of acid resistant bacteria through smearing. Then that was diluted with physiological saline containing 10% tween 80, turbidimetry was conducted with an McFarland standard turbidimetry tube (Guangdong Huankai Microbiological technology Co., Ltd.). A $10^{-2}$ mg/mL bacterium solution was prepared, and a culture medium containing a detection drug was inoculated with the bacterium solution.

Negative and positive controls are arranged in each batch of tests. A negative control comprises a drug-free culture medium. A positive control comprises *Mycobacterium tuberculosis* standard strains H37Rv. An inoculation volume of each tube is 0.1 mL. Culture was conducted with the inoculated culture medium at the temperature of 37 DEG C.

TABLE 2

Dosages of antituberculotics added into culture medium

| Drug | Culture medium drug-containing high concentration (μg/ml) | Culture medium drug-containing low concentration (μg/ml) |
|---|---|---|
| Isoniazid | 1 | 0.2 |
| Rifampicin | 250 | 50 |
| Carrimycin | 20 | 1 |

Note:
use amounts of first-line drugs in experiments of the present discloser are designed according to clinical actual use amounts.

3) Result Observation and Judgment

Observation was performed once 3 days after bacterium solution inoculation, then, observation was performed once per week, and a result was reported in 4 weeks. A culture result is judged according to the following standards:

(1) reporting that *Mycobacterium* culture is negative (−) if growth of bacterial colonies is absent through 8 weeks of culture;

(2) reporting that *Mycobacterium* is positive, and number of bacterial colonies if the number of bacterial colonies grown on a slant face of a culture medium is 20 or less;

(3) reporting that the *Mycobacterium* is positive (1+) if the bacterial colonies dispersedly grow on the slant face of the culture medium and account for ¼ or less of the area of the slant face and the number of the bacterial colonies is 20 or more;

(4) reporting that the *Mycobacterium* culture is positive (2+) if the bacterial colonies dispersedly grow on the slant face of the culture medium and account for ¼ or more of the slant face and ½ or less of the slant face;

(5) reporting that the *Mycobacterium* is positive (3+) if the bacterial colonies closely grow on the slant face of the culture medium or are partially fused and account for ½ or more of the slant face and ¾ or less of the slant face; and (6) reporting that the *Mycobacterium* is positive (4+) if the bacterial colonies closely grow on the slant face of the culture medium and account for ¾ or more of the area of the slant face.

2. *Mycobacterium tuberculosis* Resistance Activity of Carrimycin

1) Clinical *Mycobacterium tuberculosis* Sensitive to Carrimycin

Among 240 clinically-separated-identified *Mycobacterium tuberculosis* strains, 172 strains were sensitive to 1 μg/ml or 20 μg/ml of carrimycin (table 3). As can be seen from table 3, 92 strains of the 172 clinically-separated strains sensitive to carrimycin have sensitivity equivalent to that of quality control strains H37Rv in a laboratory and account for 53.48% of effective strains. The other 80 strains have sensitivity obviously higher than that of the quality control strains H37Rv in a laboratory; and 54 strains are sensitive to 1 μg/ml of carrimycin and account for 31.39% of total effective bacteria. Therefore, carrimycin has better activity to the clinically-separated *Mycobacterium tuberculosis*.

TABLE 3

Clinical *mycobacterium tuberculosis* sensitive to carrimycin

| Serial number | 1 (μg/ml) | 20 (μg/ml) |
|---|---|---|
| Quality control | 4+ | − |
| Control | 4+ | |
| 1 | 4+ | − |
| 2 | 4+ | + |
| 3 | 4+ | − |
| 4 | 4+ | + |
| 5 | 4+ | − |
| 6 | 4+ | − |
| 7 | 4+ | + |
| 8 | 4+ | − |
| 9 | 4+ | − |
| 10 | 4+ | + |
| 11 | 4+ | + |
| 12 | + | − |
| 13 | 4+ | + |
| 14 | 4+ | − |
| 15 | 4+ | − |
| 16 | − | − |

TABLE 3-continued Clinical *mycobacterium tuberculosis* sensitive to carrimycin

| Serial number | 1 (μg/ml) | 20 (μg/ml) |
|---|---|---|
| 17 | 4+ | + |
| 18 | 4+ | + |
| 19 | + | − |
| 20 | 4+ | − |
| 21 | 4+ | − |
| 22 | 4+ | − |
| 23 | 4+ | − |
| 24 | 4+ | + |
| 25 | 4+ | + |
| 26 | 4+ | − |
| 27 | 4+ | − |
| 28 | 4+ | − |
| 29 | 4+ | + |
| 30 | 4+ | + |
| 31 | 4+ | + |
| 32 | + | − |
| 33 | + | − |
| 34 | 4+ | − |
| 35 | 4+ | − |
| 36 | 4+ | + |
| 37 | + | − |
| 38 | − | − |
| 39 | 4+ | − |
| 40 | 4+ | − |
| 41 | 4+ | − |
| 42 | 4+ | − |
| 43 | 4+ | − |
| 44 | 4+ | − |
| 45 | 4+ | − |
| 46 | 4+ | − |
| 47 | 4+ | − |
| 48 | 4+ | − |
| 49 | 4+ | − |
| 50 | 4+ | − |
| 51 | 4+ | − |
| 52 | 4+ | − |
| 53 | 4+ | − |
| 54 | 4+ | − |
| 55 | 4+ | − |
| 56 | 4+ | − |
| 57 | 4+ | − |
| 58 | − | − |
| 59 | 4+ | − |
| 60 | 4+ | − |
| 61 | 4+ | − |
| 62 | 4+ | − |
| 63 | 4+ | − |
| 64 | 4+ | − |
| 65 | − | − |
| 66 | 4+ | − |
| 67 | 4+ | − |
| 68 | 4+ | + |
| 69 | 4+ | − |
| 70 | 4+ | − |
| 71 | 4+ | − |
| 72 | 4+ | − |
| 73 | 4+ | − |
| 74 | 4+ | − |
| 75 | 4+ | − |
| 76 | 4+ | − |
| 77 | 4+ | − |
| 78 | 4+ | − |
| 79 | 4+ | − |
| 80 | 4+ | − |
| 81 | 4+ | − |
| 82 | + | − |
| 83 | 4+ | − |
| 84 | − | − |
| 85 | − | − |
| 86 | − | − |
| 87 | − | − |
| 88 | − | − |
| 89 | + | − |
| 90 | − | − |
| 91 | − | − |

TABLE 3-continued

Clinical *mycobacterium tuberculosis* sensitive to carrimycin

| Serial number | 1 (μg/ml) | 20 (μg/ml) |
|---|---|---|
| 92 | + | − |
| 93 | − | − |
| 94 | − | − |
| 95 | − | − |
| 96 | 2+ | − |
| 97 | − | − |
| 98 | 4+ | − |
| 99 | 4+ | − |
| 100 | 4+ | − |
| 101 | 4+ | − |
| 102 | − | − |
| 103 | 4+ | − |
| 104 | 4+ | − |
| 105 | 4+ | − |
| 106 | − | − |
| 107 | 4+ | − |
| 108 | 4+ | − |
| 109 | 4+ | − |
| 110 | 4+ | − |
| 111 | 4+ | − |
| 112 | 4+ | − |
| 113 | 4+ | − |
| 114 | 4+ | − |
| 115 | 4+ | + |
| 116 | 4+ | − |
| 117 | 4+ | + |
| 118 | 4+ | − |
| 119 | 4+ | − |
| 120 | 2+ | − |
| 121 | − | − |
| 123 | − | − |
| 124 | − | − |
| 125 | − | − |
| 126 | − | − |
| 127 | + | − |
| 128 | − | − |
| 129 | − | − |
| 130 | − | − |
| 131 | − | − |
| 132 | − | − |
| 133 | − | − |
| 134 | + | − |
| 135 | − | − |
| 136 | 4+ | − |
| 137 | 4+ | − |
| 138 | 4+ | − |
| 139 | 4+ | − |
| 140 | + | − |
| 141 | 4+ | − |
| 142 | 4+ | + |
| 143 | 4+ | − |
| 144 | 4+ | − |
| 145 | 4+ | − |
| 146 | 4+ | − |
| 147 | 4+ | 2+ |
| 148 | − | − |
| 149 | 4+ | − |
| 150 | 4+ | − |
| 151 | 4+ | + |
| 152 | 4+ | − |
| 153 | 4+ | − |
| 154 | 4+ | − |
| 155 | 4+ | + |
| 156 | 4+ | + |
| 157 | − | − |
| 158 | 2+ | − |
| 159 | − | − |
| 160 | − | − |
| 161 | 4+ | − |
| 162 | − | − |
| 163 | − | − |
| 164 | − | − |
| 165 | − | − |
| 166 | 3+ | − |
| 167 | − | − |

TABLE 3-continued

Clinical mycobacterium tuberculosis sensitive to carrimycin

| Serial number | 1 (μg/ml) | 20 (μg/ml) |
|---|---|---|
| 168 | − | − |
| 169 | 4+ | − |
| 170 | − | − |
| 171 | − | − |
| 172 | − | − |

Quality control: laboratory standard *mycobacterium tuberculosis* strains H37Rv serve as a positive control;
Control: a drug-free culture medium. All separated strains growing in the drug-free culture medium are 4+.

2) Comparison of Activity of Carrimycin and Isoniazid to Some Clinical *Mycobacterium tuberculosis*

Activity of carrimycin and activity of clinical first-line antituberculotic, i.e., isoniazid to clinical *Mycobacterium tuberculosis* are compared, and a result shows that 20 μg/ml of carrimycin is effective to 37 isoniazid-resistant clinical *Mycobacterium tuberculosis* strains (table 4).

TABLE 4

Comparison of sensitivity of carrimycin and isoniazid to clinical mycobacterium tuberculosis

| | Isoniazid | | Carrimycin | |
|---|---|---|---|---|
| Serial number | 0.2 (μg/ml) | 1 (μg/ml) | 1 (μg/ml) | 20 (μg/ml) |
| 1 | 4+ | 4+ | 4+ | + |
| 2 | 4+ | + | 4+ | − |
| 3 | 4+ | 4+ | 4+ | − |
| 4 | 4+ | 4+ | 4+ | − |
| 5 | 4+ | 4+ | + | − |
| 6 | 4+ | 4+ | 4+ | − |
| 7 | 4+ | 4+ | 4+ | − |
| 8 | 4+ | + | 4+ | − |
| 9 | 3+ | 3+ | 4+ | − |
| 10 | 4+ | 4+ | 4+ | − |
| 11 | 4+ | 4+ | 4+ | − |
| 12 | 4+ | 4+ | 4+ | − |
| 13 | 4+ | 4+ | 4+ | − |
| 14 | 4+ | + | 4+ | − |
| 15 | 3+ | − | − | − |
| 16 | 4+ | 4+ | 4+ | − |
| 17 | 4+ | 4+ | 4+ | − |
| 18 | 4+ | 4+ | 4+ | − |
| 19 | 4+ | 4+ | 4+ | − |
| 20 | 4+ | 4+ | 4+ | − |
| 21 | 4+ | 4+ | 4+ | − |
| 22 | 4+ | 4+ | 4+ | − |
| 23 | 4+ | 4+ | 4+ | + |
| 24 | 4+ | 4+ | 4+ | + |
| 25 | 4+ | 4+ | 4+ | − |
| 26 | 4+ | 4+ | 2+ | − |
| 27 | 4+ | 4+ | 2+ | − |
| 28 | 3+ | − | − | − |
| 29 | 4+ | 4+ | − | − |
| 30 | 4+ | 3+ | 4+ | − |
| 31 | 4+ | 3+ | − | − |
| 32 | 4+ | 4+ | − | − |
| 33 | 3+ | 2+ | 3+ | − |
| 34 | 4+ | 2+ | − | − |
| 35 | 4+ | 4+ | 4+ | − |
| 36 | 4+ | 4+ | − | − |
| 37 | 3+ | − | 2+ | − |

3) Comparison of Activity of Carrimycin and Rifampicin to Some Clinical *Mycobacterium tuberculosis*

Activity of carrimycin and activity of clinical first-line antituberculotic, i.e., rifampicin to clinically-separated *Mycobacterium tuberculosis* are compared, and an experimental result shows that 20 μg/ml of carrimycin is effective to 39 rifampicin-resistant clinical *Mycobacterium tuberculosis* strains (table 5).

TABLE 5

Comparison of sensitivity of carrimycin and rifampicin to clinical mycobacterium tuberculosis

| | Rifampicin | | Carrimycin | |
|---|---|---|---|---|
| Serial number | 50 (μg/ml) | 250 (μg/ml) | 1 (μg/ml) | 20 (μg/ml) |
| 1 | 4+ | 4+ | 4+ | − |
| 2 | 4+ | 2+ | 4+ | − |
| 3 | 4+ | 4+ | 4+ | + |
| 4 | 4+ | + | 4+ | − |
| 5 | 4+ | + | 4+ | − |
| 6 | 4+ | 4+ | 4+ | − |
| 7 | 4+ | + | 4+ | − |
| 8 | 4+ | 4+ | 4+ | + |
| 9 | 4+ | − | + | − |
| 10 | 4+ | 4+ | 4+ | − |
| 11 | 4+ | 4+ | 4+ | − |
| 12 | 4+ | − | − | − |
| 13 | 4+ | 4+ | 4+ | + |
| 14 | 4+ | 4+ | 4+ | + |
| 15 | 3+ | + | − | − |
| 16 | 3+ | + | − | − |
| 17 | 4+ | + | 4+ | − |
| 18 | 2+ | + | 4+ | − |
| 19 | 4+ | 4+ | − | − |
| 20 | 4+ | 4+ | 4+ | − |
| 21 | 4+ | 4+ | 4+ | − |
| 22 | 4+ | + | 4+ | − |
| 23 | 4+ | 4+ | 4+ | − |
| 24 | 2+ | + | 4+ | − |
| 25 | 4+ | 4+ | − | − |
| 26 | 4+ | 4+ | 4+ | − |
| 27 | 4+ | + | 4+ | − |
| 28 | 4+ | 4+ | 4+ | + |
| 29 | 2+ | − | + | − |
| 30 | 4+ | − | 2+ | − |
| 31 | 4+ | − | 2+ | − |
| 32 | 4+ | + | − | − |
| 33 | 2+ | − | − | − |
| 34 | 2+ | − | − | − |
| 35 | 4+ | − | − | − |
| 36 | 4+ | 2+ | − | − |
| 37 | 4+ | − | − | − |
| 38 | 4+ | 4+ | − | − |
| 39 | 3+ | + | 2+ | − |

The activity of carrimycin to some clinical *Mycobacterium tuberculosis* is superior to that of 250 μg/ml of rifampicin.

4) Comparison of Activity of Carrimycin to Some Isoniazid-Resistant and Rifampicin-Resistant Clinical *Mycobacterium tuberculosis*

Activities of carrimycin against isoniazid-resistant and rifampicin-resistant clinical *Mycobacterium tuberculosis* are compared, and an experimental result shows that the activity of 20 μg/ml of carrimycin against 23 clinical *Mycobacterium tuberculosis* strains is superior to that of 1 μg/ml of isoniazid and that of 250 μg/ml of rifampicin (table 6).

TABLE 6

Comparison of activity of carrimycin to some isoniazid-resistant and rifampicin-resistant clinical *mycobacterium tuberculosis*

| Serial number | Isoniazid 0.2 (µg/ml) | Isoniazid 1 (µg/ml) | Rifampicin 50 (µg/ml) | Rifampicin 250 (µg/ml) | Carrimycin 1 (µg/ml) | Carrimycin 20 (µg/ml) |
|---|---|---|---|---|---|---|
| 1 | 4+ | 4+ | 2+ | + | 4+ | − |
| 2 | 4+ | + | 4+ | + | 4+ | − |
| 3 | 4+ | 4+ | 4+ | + | 4+ | − |
| 4 | 4+ | 4+ | 4+ | − | + | − |
| 5 | 4+ | 4+ | 4+ | 4+ | 4+ | − |
| 6 | 4+ | 4+ | 4+ | 4+ | 4+ | + |
| 7 | 3+ | + | 3+ | + | − | − |
| 8 | 4+ | − | 3+ | + | − | − |
| 9 | 3+ | 3+ | 2+ | + | 4+ | − |
| 10 | 4+ | 4+ | 4+ | 4+ | 4+ | − |
| 11 | 4+ | 4+ | 4+ | 4+ | 4+ | − |
| 12 | 4+ | 4+ | 2+ | + | 4+ | − |
| 13 | 3+ | − | 4+ | 4+ | − | − |
| 14 | 4+ | 4+ | 4+ | 4+ | 4+ | − |
| 15 | 4+ | 4+ | 4+ | + | 4+ | − |
| 16 | 4+ | 4+ | 4+ | 4+ | 4+ | + |
| 17 | 3+ | − | 4+ | + | − | − |
| 18 | 4+ | 4+ | 2+ | − | − | − |
| 19 | + | − | 2+ | − | − | − |
| 20 | 4+ | 4+ | 4+ | − | − | − |
| 21 | 4+ | 2+ | 4+ | − | − | − |
| 22 | 4+ | 4+ | 4+ | 4+ | 4+ | − |
| 23 | 3+ | − | 3+ | + | 2+ | − |

Proven by experimental research results of the present disclosure, carrimycin not only has activity to sensitive bacteria of clinical first-line antituberculotics, i.e., isoniazid and rifampicin, but also has activity to part of drug-resistant bacteria of the isoniazid and the rifampicin. And thus, new use of carrimycin in clinical treatment of drug-resistant *Mycobacterium tuberculosis* infected diseases is advantageously achieved.

The invention claimed is:

1. A method for treating *Mycobacterium tuberculosis* infection, consisting essentially of administering an effective amount of carrimycin to a subject.

2. The method according to claim 1, wherein carrimycin is prepared into an oral formulation, an injection formulation or any other suitable formulation for treating *Mycobacterium tuberculosis* infection.

3. A method for treating *Mycobacterium tuberculosis* infection, comprising administering an effective amount of a composition consisting of carrimycin and a pharmaceutically acceptable carrier to a subject.

4. The method according to claim 3, wherein the composition is prepared into an oral formulation, an injection formulation or any other suitable formulation for treating *Mycobacterium tuberculosis* infection.

* * * * *